United States Patent [19]

Thompson et al.

[11] Patent Number: 5,424,192
[45] Date of Patent: Jun. 13, 1995

[54] MARKERS FOR INVASIVE PROSTATIC NEOPLASIA

[75] Inventors: Timothy C. Thompson, Houston; Thomas P. Dooley, San Antonio, both of Tex.

[73] Assignee: Baylor College of Medicine, Houston, Tex.

[21] Appl. No.: 38,491

[22] Filed: Mar. 29, 1993

[51] Int. Cl.⁶ .................... G01N 33/574; G01N 33/53
[52] U.S. Cl. ................................... 435/7.23; 435/7.9; 435/7.92; 436/512; 436/518; 436/64; 436/63; 436/813
[58] Field of Search ...................... 435/7.23, 7.9, 7.92; 436/512, 518, 64, 813, 63

[56] References Cited

PUBLICATIONS

Aumuller, G., et al., *Prostate*, vol. 17, No. 1, pp. 31–40, 1990.
Abrahamsson, P. A., et al., *Prostate*, vol. 12, No. 1, pp. 39–46, 1988.

*Primary Examiner*—Toni R. Scheiner
*Attorney, Agent, or Firm*—Baker & Botts

[57] ABSTRACT

This invention is directed to the identification, isolation and use of nonprostate derived markers, such as markers derived from the seminal vesicles, and antibodies which recognize these markers in the diagnosis of invasive proatic neoplasia, to diagnostic aids for screening biological samples for evidence of invasive prostatic neoplasia, and to methods for the use of these diagnostic aids.

34 Claims, 3 Drawing Sheets

MARKERS FOR INVASIVE PROSTATIC NEOPLASIA

BACKGROUND OF THE INVENTION

1. Field of the Invention

This invention relates to the identification, isolation and use of markers and antibodies which recognize these markers in the diagnosis of invasive prostatic neoplasia in humans, and to diagnostic aids for screening biological samples for evidence of invasive prostatic neoplasia.

2. Description of the Background

The prostate, an organ of the mammalian male urogenital system, is located at the base of the bladder surrounding the urethra. Although encapsulated, the walnut-sized prostate can be divided into five lobes, the posterior, middle, and exterior lobes and two lateral lobes. Histological examination reveals that the prostate is a highly microvascularized gland comprising fairly large glandular spaces lined with epithelium. The majority of fluid of the male ejaculate is supplied by this gland and the seminal vesicles.

The prostate is an endocrine-dependent organ which responds to both the major male hormone, testosterone, and the major female hormones, estrogen and progesterone. In particular, the testicular androgen is believed important for prostate growth and development because, in both humans and other animals, castration leads to prostate atrophy and an absence of any incidence of prostatic carcinoma.

There are two major neoplasia of the prostate, benign enlargement of the prostate or nodular hyperplasia (also called benign prostatic hyperplasia (BPH) or benign prostatic hypertrophy), and prostatic carcinoma. Nodular hyperplasia is very common in men over the age of 50. It is characterized by the presence of a number of large distinct nodules in the periurethral area of the prostate. Although benign, these nodules can produce obstruction of the urethra causing nocturia, micturition, and difficulty in starting and stopping a urine stream upon voiding the bladder. Occasionally, catheterization is required and even surgery. In the more extreme cases, secondary changes in the bladder can occur such as hypertrophy, acute retention with secondary urinary tract involvement, azotemia and uremia. Although all of these changes of the prostate may suggest pre-malignancy, there is as yet no direct association between nodular hyperplasia and prostatic carcinoma.

Carcinoma of the prostate is the most common form of cancer in human males with upwards of one third of those cases being fatal. In the more aggressive forms, transformed prostatic tissue escapes from the prostate capsule invading locally and throughout the bloodstream. Local invasions typically involve the seminal vesicles, the base of the urinary bladder, and the urethra. Hematogenous spread occurs primarily to the bones and lymph nodes, but can include massive visceral invasion as well. Histologically, most lesions are adenocarcinomas with well-defined gland patterns, but the more typical malignancy patterns associated with the very aggressive cancers are also common. Except in rare instances, all forms of prostatic carcinoma originate in the peripheral zone of the gland which is palpable upon rectal examination.

Prostatic carcinomas are graded and staged by number and letter according to histological criteria, the arrangement and appearance of malignant glands, and the degree of anaplasia of the cancerous cells. Stage A1 tumors include the incidental or clinically unsuspected cancers. These are detected in autopsy and rarely pose a problem to the patient. Stage B tumors are detectable by rectal digital examination and are also confined to the prostate. Tumors classified as B1, B2, and so on, indicate increasing severity of tumor formation. These tumors are fairly common in older men who begin to show signs and symptoms characteristic of some form of prostatic carcinoma. Stage C tumors have breached the prostate capsule and may or may not have invaded the surrounding tissues such as the seminal vesicles. Those tumors which have seminal vesicle involvement show an 80% correlation with lymph node involvement (C2). Stage D tumors have distinct metastases and a 100% correlation with lymph node involvement. Over 75% of patients with prostatic carcinoma show signs of stage C or D type development with significant urinary tract involvement. Only 5–10% of stage A patients, of those who have been followed for 8–10 years, develop stage C or D type prostatic carcinoma although the probability increases for patients who first present at a fairly young age. Young males with nodular hyperplasia are typically recommended for surgery or more aggressive endocrine therapy.

Little is known about the causes of prostatic carcinoma, but there are at least three confirmed risk factors—age, race and endocrine system. As discussed, the incidence of all forms of prostatic neoplasia is very high in men over 50. In the 45–49 year old age group the incidence is about 4.8 per one hundred thousand men and increases to 513 between the ages of 70 to 75. The incidence of latent carcinoma is higher still. Over 30% of prostate tissue in autopsied males over 50 shows some sign of latent carcinoma.

The second risk factor, race, is fairly strong. Among white males in the United States the incidence of prostatic neoplasia in those over 50 is about 58 per one hundred thousand men. The rate increases to about 95 per one hundred thousand in black males whereas in oriental males, prostatic neoplasia is rather rare at about 3 to 4 per one hundred thousand in one study performed in Hong Kong. The exact reason for this distribution is unclear. Although environmental effects should not be discounted, epidemiology points to a strong genetic influence.

The final risk factor, the endocrine system, may be the most important. Although, no direct link has been established between absolute or relative levels of any hormone and neoplasia of the prostate, the evidence for some form of hormonal regulation is convincing. First, in both humans and dogs, the only other mammal known to develop hyperplasia with aging, nodular hyperplasia or full-blown carcinoma of the prostate only develop in the presence of intact testes. Secondly, in castrated young dogs it is possible to induce nodular hyperplasia by administering of androgen and estradiol, suggesting that hormones produced by the testes are required for prostate development. Further, there is some evidence that dihydrotestosterone, which is derived from testosterone, may be the ultimate mediator of cell growth. Prostate cells of the epithelium are covered with dihydrotestosterone receptors which increase in number in the presence of estrogen. In men and dogs, plasma testosterone levels decrease and estradiol levels increase with age. This alteration shifts the hormonal balance of the cells and possibly sensitizes the prostate for transformation. At the very least, it appears that androgens are required to maintain the viability of prostate epithelium from which most carcinomas derive.

Yearly rectal examination is very useful for the early detection of prostatic neoplasia. This detection method is fairly simple and straightforward. However, it is subject to bias and not very well standardized. At the earliest, it can only detect stage B carcinoma and has no capacity to determine whether stages C or D are developing. Further, the digital rectal exam is not very sensitive. Approximately 30-60% of men have a prostatic neoplasia that cannot be detected by the physician, which is further complicated by the fact that these men usually present with no symptoms at all. A number of new techniques look promising. These include ultrasound and other methods of noninvasive detection such as positron emission tomography (PET). These methods are limited to the detection of formed tumors and are unable to detect prostatic carcinoma which is just beginning to invade surrounding tissue.

Chemotherapy, surgery or radiotherapy is the treatment of choice for stage A or B prostatic neoplasia. Surgery involves complete removal of the entire prostate, radical prostatectomy, and often removal of the surrounding lymph nodes, lymphadenectomy. Radiotherapy may be either external or interstitial using $^{125}$I and is typically performed in conjunction with surgery. Endocrine therapy is the treatment of choice for more advanced forms. The aim of this therapy is to deprive the prostate cells, and presumably the transformed prostate cells as well, of testosterone. This is accomplished by administering estrogens or synthetic hormones which are agonists of luteinizing hormone-releasing hormone (LHRH). These cellular messengers directly inhibit testicular and organ synthesis and suppress luteinizing hormone (LH) secretion which in turn leads to reduced testosterone secretion by the testes. Despite the advances made in achieving a pharmacologic orchiectomy, the survival rates for those with stage C and D carcinomas are rather bleak. In the short term, the most promising results will be achieved by earlier detection using more sensitive assays.

Carcinoma cell invasion of the seminal vesicles is a very poor prognosis for the patient. As discussed, seminal vesicle involvement frequently correlates with metastases to the lymph nodes and subsequent dissemination throughout the body. Invasion of the seminal vesicles begins with cell multiplication at the base of the prostate. Transformed cells expand within and through the ejaculating duct, localizing in the seminal vesicles near their point of junction with the vas deferens (A. A. Villers et al., J. Urol. 143:1183, 1990). Surprisingly, others have found a relatively low frequency of positive nodes in patients with seminal vesicle invasion, but a comparable prognosis among patients with and without lymph node metastases (E. Mukamel et al., Cancer 59: 1535, 1987). No alternative explanation was proposed. Uncertainty in these results may stem from the fact that the seminal vesicles are not very well defined morphologically or biochemically.

There are two seminal vesicles in man, one located on each side of the urethra posterior to the urinary bladder and superior to the prostate. They are believed to contain two types of epithelial cells, principal or superficial cells, and basal cells. Each gland is open to the urethra and comprises a highly convoluted tube coiled upon itself which, if extended, would be approximately 15 cm in length. The convolutions within each gland impart a honeycomb appearance when viewed under cross section. The internal cells of the individual vesicles are highly interconnected with ridges and folds both circular and longitudinal. Individual cells of the walls contain numerous secretory bodies including golgi vacuoles, electron dense granules and droplets. These bodies secrete a mixture of materials into the lumen of each tubule. Approximately 70% of human ejaculate is composed of this material which contains fructose, citrate, inositol, prostaglandin, choline esters, and a number of soluble proteins. A few of these proteins have been identified as specific to seminal vesicle tissue including semenogelin I, a large molecular weight protein which can be broken down into three subunits of 52 kDa, 71 kDa, and 76 kDa (H. Lilja et al., J. Biol. Chem. 264:1894, 1989), semenogelin II (H. Lilja and A. Lundwall, Proc. Natl. Acad. Sci. USA 89:4559, 1992), lactoferrin or scafferin (A. Hekman and P. Rumke, Fertil. Steril. 20: 312,1969), seminal vesicle specific antigen (SVS A), MHS-5 specific antigen (J. C. Herr et al., J. Reprod. Immunol. 16:99, 1989), rat seminal vesicle specific (SVS) proteins I-VIII (J. Seitz and G. Aumuller, Andrologia 22:25, 1990), B-microseminoprotein (B-MSP) (K. Akiyama et al., Biochim. Biophys. Acta 829:288, 1985), and seminal plasma number 7 antigen (K. Koyama et al., J. Reprod. Immunol. 5:134, 1983). These proteins and antigens are only now being analyzed in detail and some have been cloned by recombinant DNA techniques.

Fairly recently, a number of serum antigens have been characterized as markers for prostatic neoplasia. These markers are useful because they are relatively straightforward to assay using noninvasive procedures and may detect prostatic neoplasia at very early stages of development. Both malignant and normal prostate epithelial cells were found to express a prostate-specific acid phosphatase (PAP) which is detectable in serum by biochemical and other immunological techniques. Elevated PAP levels correlate well with neoplasia that has spread beyond the prostate capsule. Consequently, PAP is a useful serum marker for characterizing the later stages of prostatic neoplasia and also for monitoring the progress of the disease in patients.

Another marker which has proved to be of value is the prostate-specific antigen (PSA), a serine protease found in both normal and neoplastic prostate epithelium. Investigations have determined that there is a direct correlation between serum PSA levels with the size and stage of a tumor. The normal concentration of PSA in men is from 0 to 2.8 ng/ml of serum. In one study, researchers determined that average PSA concentrations in the serum of patients grouped according to severity were proportional to the clinical state of the tumor (T. A. Stamey, et al., N. Engl. J. Med. 317:909, 1987). These authors did not indicate whether PSA levels could be used to determine the pathological stage of carcinoma in individual patients. Concentrations of 40 ng/ml were predictive of advanced stages of disease, but the predictive value of serum concentrations of less then 15 ng/ml were less than clear. PSA titers were only marginally useful to distinguish whether the tumor was contained by or had escaped the prostate. Levels greater than 10 ng/ml were typical in patient groups with more advanced and gland-unconfined carcinomas. However, it was not atypical to find high PSA levels in patient groups with gland-confined hyperplasia.

These theories were partly confirmed in a more recent study which looked at serum PSA levels in 209 men with various stages of prostatic neoplasia (T. E. Osterling et al., J. Urol. 139:766, 1988). These authors determined that PSA levels showed a statistically significant correlation with pathological stages when compared within the various groups. However, the levels were far less useful when looking at patients on an individual basis. There was a large degree of variability between patient groups and a significant number of both false and missed positives. In a rigorous analysis using greater numbers of men and taking into account actual or predicted numbers of carcinoma cells, Partin et al. determined that serum PSA levels were influenced by tumor volume and the stage of differentiation (A. W. Partin et al., J. Urol. 143:747, 1990). Mean antigen levels increased with advanced pathological stage, but this seemed to be related more to overall tumor volume than to any particular stage of the disease. In fact, immunohistochemical studies revealed that higher stage tumors actually produced less PSA, possibly due to the diseased state of the cells. The authors concluded that PSA levels are unreliable for preoperative prediction of the pathological stage of individual patients.

A number of other prostate antigens have since been identified. The most well-studied of these has been the prostatic carcinoma associated complex (PAC) also called the glycoprotein complex (G. L. Wright et al., Int. J. Cancer 47:717, 1991). Although specific for prostatic epithelium, this protein complex of 35–310 kDa antigens was not correlative for the staging of prostatic carcinoma.

SUMMARY OF THE INVENTION

The present invention overcomes the problems and disadvantages associated with current strategies and designs and provides a new method for stagespecific detection of prostatic neoplasia in a patient.

As broadly described herein, one embodiment of the invention is directed to a method for identifying, isolating, and using markers derived from non-prostatic tissues such as the seminal vesicles in the detection of prostatic neoplasia in a patient. The marker may comprise a protein or an antigenic part of a protein. This invention also encompasses the identification, isolation and cloning of the gene or genes which code for the specific marker. The recombinant gene or genetic sequence is used to express recombinant marker or antigenic parts of the marker.

As broadly described herein, another embodiment of the invention is directed to methods for the identification and isolation of antibodies to seminal vesicle-specific markers and other non-prostatic markers in biological samples. Marker is incubated with a biological sample taken from a patient suspected of having prostatic neoplasia. The sample may be tissue, blood, urine, or semen. The amount of serum-derived antibody which binds to the marker is determined and, if over a predetermined base level, indicates the presence of specific antibody in the sample and prostatic neoplasia in the patient.

As broadly described herein, a further embodiment of the invention is directed to an antibody which specifically binds to the marker and to a method for using this antibody to detect prostatic neoplasia in a patient. The antibody may be a monoclonal or polyclonal antibody or a fragment of a monoclonal or polyclonal antibody such as an Fv fragment and preferably the antibody is an IgG isotype. In one aspect of the invention the specific antibody is incubated with a biological sample taken from the patient suspected of having prostatic neoplasia. The sample may be tissue, blood, urine, or semen. The amount of specific marker in the sample which binds to the antibody is determined and if over a predetermined base level indicates the presence of specific marker in the sample and prostatic neoplasia in the patient.

As broadly described herein, a still further embodiment of the invention is directed to diagnostic kits for the detection of prostatic neoplasia in a patient comprising the marker or the marker-specific antibody and methods for using these markers and antibodies for the detection of prostatic neoplasia.

Other objects and advantages of the invention are set forth in part in the description which follows, and in part, will be obvious from this description, or may be learned from the practice of the invention.

DESCRIPTION OF THE INVENTION

Figure 1:
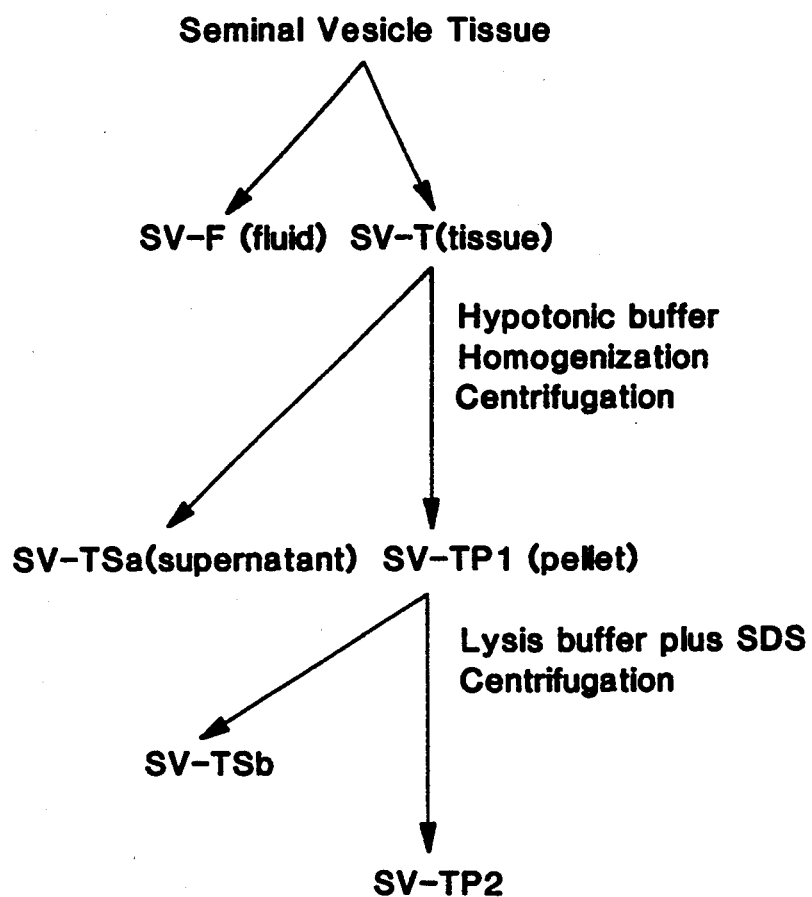
FIG. 1 Diagrammatic representation of a fractionation protocol for seminal vesicle tissue.

To achieve the objects and in accordance with the purposes of the invention, as embodied and broadly described herein, the present invention comprises markers, parts of markers, genes and genetic sequences which encode these markers, both monoclonal and polyclonal antibodies and parts of antibodies, and diagnostic kits for the detection of prostatic neoplasia in a patient.

Neoplasia of the prostate can be divided into two basic forms, nodular hyperplasia and carcinoma. Nodular hyperplasia is not a serious health concern. For those with asymptomatic hyperplasia, no treatment is necessary. For those with symptomatic hyperplasia of the prostate, therapy typically involves chemotherapeutic drugs, radiation therapy, or radical prostatectomy. Prostatic neoplasia only becomes life threatening when transformed prostate cells break through the prostate capsule and metastasize throughout the body. Therefore, it is the invasion-proficient status which is most important in the detection of this disease.

The seminal vesicles are often invaded by prostatic carcinoma cells. Upon invasion this normally highly organized and compartmentalized structure becomes damaged. Damage due to physical disruption of the seminal vesicles results in the presentation of novel seminal vesicle-derived markers to the blood stream and other bodily fluids. In one aspect of the invention, these disrupted and damaged cells passively release seminal vesicle-specific macromolecules, or markers, which may be proteins, cytokines, modified proteins, peptides, complex biochemicals, fragments of proteins or peptides, nucleic acids, or modifications or combinations thereof, to areas of the body such as, for example, the bloodstream. In another aspect, the damaged and "leaky" vasculature produced by the invading carcinoma leads to the direct release of seminal vesicle secretions into areas of the body such as, for example, the semen, urine or bloodstream. In either situation, once released, these markers may be detectable by biochemical techniques known to those of ordinary skill in the art.

These seminal vesicle-derived markers are also likely to be highly antigenic. The patient's lymphocytes will produce antibodies specific to these "newly-recognized" seminal vesicle-derived antigens. Although the seminal vesicles are not foreign to the patient, antigens released have not previously been exposed to the host's immune system and could stimulate a humoral or cellular response. These host-derived, antigen-specific antibodies and/or antigen-primed cells may also be detectable by biochemical techniques known to those of ordinary skill in the art. Upon detection and quantitation, the absolute or relative amounts of seminal vesicle-specific antigens or antibodies may be determinative of a particular stage of prostatic neoplasia. These results may be used alone or in combination with PAP and/or PSA titers to select or rule out a course of therapy for a patient.

A first embodiment of the invention is directed to the identification of seminal vesicle-specific markers, which may be proteins, cytokines, modified proteins, peptides, complex biochemicals, fragments of proteins or peptides, nucleic acids, or modifications or combinations thereof, and are useful for the detection of prostatic neoplasia. First, seminal vesicle-specific markers are identified and isolated. For example, seminal vesicles or tissue samples containing seminal vesicle-specific markers such as blood, semen, or urine are obtained. In a direct approach, seminal vesicle tissue is isolated by necropsy from, for example, human cadavers or by radical prostatectomy. Samples may be used immediately or frozen to −80° C. for later use.

Samples are fractionated by, for example, chromatography, such as ion-exchange or affinity column chromatography, salt fractionation using for example ammonium sulfate precipitation, centrifugation, size and chemical fractionation, SDS-polyacrylamide gel electrophoresis (PAGE) run under reducing or non-reducing conditions, or filtration. Using such techniques, particular fractions or extracts containing, for example, the glycoprotein-rich secretory markers, can be targeted. Alternatively, or in addition to these procedures, more rigorous techniques can be used to isolate single markers or antigens or groups of markers, such as high-performance liquid chromatography (HPLC), reversed-phase HPLC, ion exchange HPLC, fast-phase liquid chromatography (FPLC), one-, two-, or three-dimensional electrophoresis followed by electro-elution or electrotransfer of the markers of interest from the electrophoresis matrix onto a membrane such as a nitrocellulose membrane. These and other so-called conventional techniques for the isolation of proteins and peptides are described in *Proteins: Structures and Molecular Properties* (T. E. Creighton, Freeman and Co., N.Y., 1984), and *A Practical Guide to Protein and Peptide Purification for Micro Sequencing* (P. T. Matsudaira, Academic Press, N.Y., 1989), which are hereby specifically incorporated by reference.

In an indirect-approach, seminal vesicle tissue can be used to create antibodies specific to seminal vesicle markers which are used to identify and isolate those antigenic markers. For example, seminal vesicle tissue or biological samples from patients with suspected or confirmed cases of some form of prostatic neoplasia are treated to isolate fractions which are likely to contain seminal vesicle-specific markers. These include, for example, fractions of cell surface antigens, glycoproteins, and lipoproteins, or fractions of cells disrupted to release membrane-associated and cytoplasmic antigens. Each of these fractions is injected into a female laboratory animal, such as a rabbit, a guinea pig, a rat or a mouse, to create seminal vesicle-specific polyclonal or monoclonal antibodies. Female animals are chosen as these are believed to have the lowest probability of containing anti-seminal vesicle antibodies and the highest probability of generating a strong immune response. After injection and possibly the administration of booster injections, blood is collected and polyclonal antisera and/or antibodies are isolated from the serum. If necessary, seminal vesicle specific antibodies can be purified using, for example, affinity chromatography.

Monoclonal antibodies are also prepared. About three to four weeks after the initial injections, spleen cells are isolated, fused with myeloma cells of the same or a different species, such as for example, the murine cell lines P3-X63 Ag8, X63Ag.653, SP2/0-Ag14, FO, NSI/1-Ag4-1, NSO/1, and FOX-NY, or the rat cell lines Y3-Ag.1.2.3, YB2/0, and IR983F, and screened for hybridomas which express seminal vesicle-specific monoclonal antibodies. Hybridomas expressing human antibody or mostly human antibody can be creating by fusing the spleen cells obtained with human myeloma or human heteromyeloma cells such as, for example, U-266, FU-266, and HFB-1. A fusion procedure which employs polyethylene glycol or Epstein-Barr virus is preferred. Methods for the creation of antigen-specific polyclonal and monoclonal antibodies are disclosed in *Antibodies: A Laboratory Manual* (E. Harlow and D. Lane, Cold Spring Harbor, 1988). These antibodies are used to detect markers which are specific to seminal vesicles by immunoprecipitation, immunoblotting, such as Western blotting of electrophoresed seminal vesicle-specific antigens, or affinity chromatography.

Alternatively, seminal vesicle-specific markers, which may be purified, partially purified, or recombinantly produced, can be used to identify and isolate seminal vesicle-specific antibodies in, for example, the blood stream of patients. Seminal vesicle-specific markers are coupled to a matrix such as, for example, sepharose, sephadex, sephacel, or sephacryl, using techniques which are known to those of ordinary skill in the art. Whole blood or preferably blood plasma is subjected to, for example, affinity column chromatography using the antigert-coupled matrix. Fractions comprising seminal vesicle-specific antibodies are eluted and further purified using affinity chromatography with a purified antigen-coupled matrix or using conventional techniques such as differential centrifugation or other known separation techniques.

Seminal vesicle-specific markers which are identified and isolated, at least partially, are characterized. Their molecular weight is determined by, for example SDS-PAGE. The isoelectric point is determined by 2-dimensional PAGE techniques such as isoelectric focusing. The amino acid sequence is determined by, for example, partial digestion of the purified antigen, if necessary, automated sequence analysis of the digestion products, and reconstruction of the complete sequence from the resulting data. The presence or absence of lipids, carbohydrates, unusual amino acid residues, polysaccharide and other modifications is also determined. From knowledge of the complete sequence of a macromolecule, such as a protein or peptide, hydrophobicityhydrophilicity charts can be determined, particularly antigenic regions identified, and three-dimensional structures predicted. Once characterized, these markers are compared with other known seminal vesicle-specific molecules either by computer sequence alignment analysis or by direct comparison of know features and, if necessary, side-by-side characterization.

With knowledge of even a portion of the amino acid sequence of the marker, it is possible to determine the genetic sequence with codes for the entire marker and to clone this sequence from the cellular genome or chemically synthesize all or part of the gene. To clone the gene, a genomic or cDNA library is created and probed with the genetic sequence of interest, which may be chemically synthesized or isolated from a genetic library. Positive clones are picked, expanded, and expressed to identify their products. In this fashion, an entire gene can be cloned from a cellular genome and expressed in a recombinant expression vector. Alternatively, using polyclonal or monoclonal antibodies, cDNA expression libraries can be probed for seminal vesicle-specific markers directly. The positive clones are identified, expanded, and their recombinant DNA sequences subcloned using techniques which are well known for those of ordinary skill in the art such as, for example, those described in *Current Protocols in Molecular Biology* (F. M. Ausubel et al., Green Publishing Assoc. and Wiley-Interscience, 1989), and *Molecular Cloning: A Laboratory Manual, 2nd Ed.* (J. Sambrook et al., Cold Spring Harbor Laboratory, N.Y., 1989), which are hereby specifically incorporated by reference. Recombinant vectors containing all or specific antigenic portions of the gene of interest are created and used to produce large quantities of recombinant expression product in prokaryotes, such as, for example, *E. coli*, eukaryotes such as, for example, Bacculovirus, plant cells, or animal cells, or yeast cells. The amino acid sequence of the gene of interest is also synthesized chemically to produce large quantities of marker and to isolate additional marker.

Markers, including antibodies, antigens, and antibody or antigen fragments produced accordingly are useful in diagnostic kits for the detection of invasive prostatic neoplasia. As discussed, invasive prostatic neoplasia may be associated with release of seminal vesicle-specific antigens into areas of the body which do not normally receive these antigens, such as, for example, the bloodstream, the bladder, or the passageways of the male urogenital system such as the vas deferens, the bulbourethral gland, or the urethra. A sample of biological fluid, such as, for example, a tissue sample, or a sample of biological fluid such as semen, urine or blood, taken from the patient suspected of having prostatic neoplasia is analyzed for the presence or the increased presence of one or more of these seminal vesicle-specific markers or antigens or for the presence or increased presence of human antibodies directed against such markers or antigens.

Another embodiment of the invention is the analysis of samples of tissue or biological fluid obtained from patients suspected of having prostatic neoplasia for the presence of seminal vesicle-specific antigens as markers for invasive prostatic neoplasia. Useful assays include, for example, an enzyme immune assay (EIA) such as an enzyme-linked immunosorbent assay (ELISA), a radioimmune assay (RIA), a Western blot assay, or a slot blot assay. Briefly, samples of biological fluid believed to contain one or more markers of invasive prostatic neoplasia are incubated with seminal vesicle-specific antibody prepared according to the invention. The antibody may be of any isotype including $IgG_1$, $IgG_{2a}$, $IgG_{2b}$, IgM, IgA, or IgD, but an IgG is preferable. Optionally, the antibody, which may be polyclonal, monoclonal, or a fragment of a monoclonal or polyclonal antibody, preferably the Fv fragment, may be fixed to a solid support to facilitate washing and subsequent isolation of the complex. Examples of solid supports include glass or plastic such as, for example, a tissue culture plate, a vial, a microtiter plate, a stick, a paddle, a bead, or a microbead. After incubation, the mixture is washed and the amount of antibody-antigen complex formed determined. This is accomplished by incubating the washed mixture with a second, labeled antibody which is specific to the complex. This second antibody may be a monoclonal or polyclonal antibody and is labeled with a detectable label. Examples of detectable labels include a radio isotope, a stable isotope, a fluorescent chemical, a luminescent chemical, a metal, an electrical charge, an enzyme, a chromatic chemical, a spatial chemical, an electron-dense molecule, or a label detectable by mass spectrometry. Alternatively, the amount of seminal vesicle-specific antigert in the sample may be determined using an indirect assay, wherein, for example, a second, labeled antibody is used to detect bound seminal vesicle-specific antibody, and/or in a competition or inhibition assay wherein, for example, a monoclonal antibody which binds to a distinct epitope of the antigen are incubated simultaneously with the mixture. Each of these assays are well known to those of ordinary skill in the art and described in, for example, *Antibodies: A Laboratory Manual*.

In another embodiment of the invention, a biological sample is taken from a patient suspected of having prostatic neoplasia and assayed for the presence of host antibodies to seminal vesicle-specific antigens. Useful assays include, for example, an RIA, an EIA such as an ELISA, a Western blot or a slot blot. As discussed, seminal vesicle antigens may be released into the body or blood stream upon invasion of transformed prostatic cells. These antigens may be recognized as foreign by the immune system of the body and anti-antigen antibodies produced. These host antibodies can be specifically detected using a diagnostic kit which comprises one or more purified or partially purified seminal vesicle-specific markers. As before, the assay to detect these antibodies can be a direct, indirect, competitive or inhibition assay. The assay may comprise polyclonal antibodies or fragments of polyclonal antibodies, such as the Fv fragment, or monoclonal antibodies or fragments of monoclonal antibodies, such as the Fv fragment, either of which are labeled with a detectable label such as, for example a radio isotope, a stable isotope, a fluorescent chemical, a luminescent chemical, a metal, an electrical charge, an enzyme, a chromatic chemical, a spatial chemical, an electrondense molecule, or a label detectable by mass spectrometry. The antibodies to be detected may be of any isotype including IgG, $IgG_{2a}$, $IgG_{2b}$, IgM, IgD, IgA, or a combination of these isotypes. Isotype specific anti-antibodies may also be utilized to identify or quantitate specific antibody isotypes.

In a direct assay, it is preferable that the seminal vesicle-specific antigens or antigenie fragments be produced recombinantly, although as discussed, antigens can also be produced synthetically or isolated and purified by convention techniques. It is preferred that the marker, or antigen, be fixed for a solid support such as, for example, glass or plastic such as a tissue culture plate, a vial, a microtiter plate, a stick, a paddle, a bead, or a microbead. A biological sample suspected of containing marker-specific antibody is added to the fixed antigen or marker and incubated, for example, between one hour and overnight: in phosphate-buffered saline (PBS), at between 4° C. and 37° C., preferably at about room temperature. After incubation, the mixture is removed and the solid support washed. The washed support is incubated with, for example, a labeled anti-antibody and incubated as before. The label is detectable and may be a radio isotope, a stable isotope, a fluorescent chemical, a luminescent chemical, a metal, an electrical charge, an enzyme, a chromatic chemical, a spatial chemical, an electron-dense molecule, or a label detectable by mass spectrometry. The amount of labeled antibody which binds to the solid support is determined and compared to the amount of labeled, non-specific antibody which remains bound in control assays. Control assays comprise assays that test biological samples which are known not to contain marker-specific antibody or another assay which provides a determination of background levels of antibody and/or a baseline internal negative control. If the amount of antibody bound is greater than a predetermined background or base level, the biological sample contains seminal vesicle-specific antibodies and the patient is diagnosed as likely to have invasive prostatic neoplasia.

Alternatively, the assay can be performed without washing and without separate incubation steps by using polyclonal or monoclonal antibodies. For example, using a competition assay, excess labeled antibody is added to antigens fixed to a solid support. This provides a measure of 100% binding. To another sample or series of samples, biological samples, such as samples of serum, are added to the incubation mixture and any decrease from 100% binding is indicative of the presence of seminal vesicle-specific antibodies in the sample.

This invention also comprises procedures and techniques to identify, isolate, and utilize markers derived from tissues other than the seminal vesicles for the detection of invasive prostatic neoplasia. Likely tissues include those tissues which surround and are in close proximity with the prostate such as the prostate capsule, the ejaculatory duct, the bladder, the vas deferens, the bulbourethral gland, the crus, the urethra, the corpus spongiosum, and the corpus cavernosum. Markers may be passively released upon tissue damage by the invading prostatic cells or actively released into new areas of the body. The non-prostate, non-seminal vesicle-derived markers may be proteins, cytokines, modified proteins, peptides, complex biochemicals, fragments of proteins or peptides, nucleic acids, or modifications or combinations thereof. As before, likely markers of prostate neoplasia may be identified in biological samples, such as tissue, blood, semen, or urine, and traced back to one or more of these tissues. Alternatively, these tissues can be fractionated and screened for likely markers and these markers used in diagnostic kits and methods utilizing procedures described herein. In addition, host reactions, both humoral and cellular, would occur against passively or actively released markers. Antibodies to these markers could also be detected in diagnostic kits and are also described herein.

The following examples are offered to illustrate embodiment of the present invention, but should not be viewed as limiting the scope of the invention.

EXAMPLES

Example 1 - Identification of Seminal Vesicle-Specific Markers

Seminal vesicle tissue is surgically removed from a human cadaver or removed by radical prostatectomy biopsy from a patient to a 100 mm tissue culture dish containing about 10 ml of cold (4° C.) hypertonic buffer (50 mM Tris-Cl, pH 7.0; 1.0 mM KCl; 1 mM PMSF; 10 mM EDTA; +/−1 mM DTT). Tissue is mechanically minced and/or dispersed by passage through a 19 gauge needle, followed by homogenization using either a cylindrical homogenizer or rotary tissue disrupter. The membrane fractions and soluble fractions of samples are separated by centrifugation. The pelleted fraction is suspended in hypotonic buffer plus 2% SDS and centrifugation is repeated. This process is diagrammatically outlined in FIG. 1. Optionally, lectin affinity chromatography may be used to enrich the soluble fractions for glycoproteins (as predictive for secretory proteins).

Semen, urine, and blood samples are collected from normal volunteers and patients with suspected or confirmed cases of prostatic carcinoma at various stages of severity. Semen ejaculate samples, preferably from normal vasectomized individuals, are mixed immediately with PMSF and EDTA in chilled phosphate buffered saline, pH 7.2 (PBS) or hypotonic buffer. These samples are separated into soluble and particulate fractions by pelleting at 10,000×g for 10 minutes. The particulate fraction may be suspended in hypotonic buffer and diluted as necessary to about 1 ug/100 ul in PBS. The soluble fraction may be concentrated using Amicon filters or diluted with PBS as necessary to about 1 ug/100 ul of liquid. Seminal vesicle fractions including the membrane fraction, the soluble fraction and the enriched fraction, and fractions of blood and semen are subjected to SDS polyacrylamide gel electrophoresis (PAGE) under reducing or non-reducing conditions, along with appropriate molecular weight markers and negative controls. SDS-PAGE gels have an extended longitudinal dimension (ca. 16") for enhanced band resolution. The resulting gel matrices are subjected to electrotransfer to a suitable membrane such as nitrocellulose.

Briefly, the electrophoresis matrix is equilibrated for about 30 minutes in transfer buffer (18.2 g Tris Base; 86.5 g glycine; 4.0 liters $H_2O$; 1200 ml methanol) at room temperature. Pre-wetted nitrocellulose transfer membrane is cut to size and placed on top of the gel. Pre-wetted Whatmann 3 MM filter papers are placed on both sides of the gel-nitrocellulose slab, and the entire structure placed in an electrophoresis tank of transfer buffer. Electrophoresis is begun for 30 minutes at 100 volts, turned down to 14 volts (constant voltage) and continued overnight (about 14 hours) at 4° C. Upon completion of the transfer, the membrane is removed and assayed for transfer efficiency.

Figure 2A:
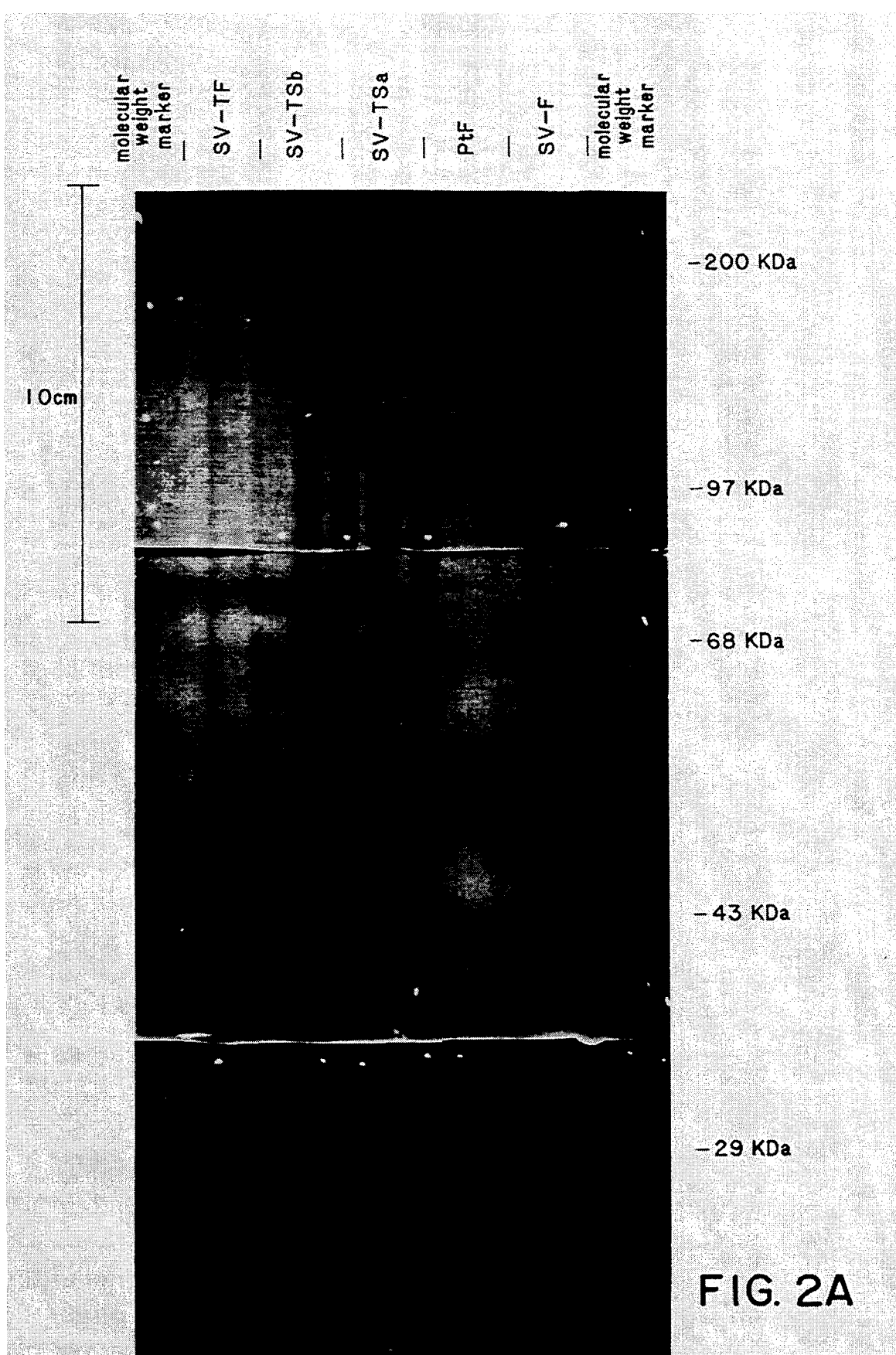
FIG. 2A Ponceau S stained nitrocellulose membrane of electrophoretically separated fractions of seminal vesicle tissue homogenate. Pr-F=prostate fluid collected at prostatectomy.

To visualize transferred proteins, membranes are placed in Ponceau S solution (0.5 g Ponceau S dissolved in 1 ml glacial acetic acid and brought to a total volume of 100 ml with $H_2O$ just before use) for 5 minutes at room temperature. The membranes are destained for 2 minutes in water and photographed using transmitted light through the stained nitrocellulose membrane. A photograph of a representative stained membrane of a high-resolution, 16" PAGE gel is shown in FIG. 2A. Bands observed on the membrane are isolated directly or the seminal vesicle-specific antigens further identified by probing the membranes with seminal vesicle-specific antibody created as follows. Briefly, fractions of seminal vesicle tissue, blood and/or semen, created above, are mixed with equal volumes of incomplete Freund's adjuvant and injected subcutaneously into female rabbits using a 25-gauge needle at a dose of about 400 ul per injection. The first antigen only is presented in complete Freund's adjuvant. Each animal receives from one to ten injections at various sites high on the dorsal flank between the ribs and the hip. Antigen injections are repeated approximately every two weeks for a minimum of three times using fresh seminal vesicle tissue materials.

After about four weeks from the initial injection, 5–10 ml samples of blood are collected by venipuncture from the rabbits' marginal ear vein using a 23-gauge needle. Blood flow is stopped by applying gentle pressure to the cut with sterile gauze for 10–20 seconds. Collected blood is allowed to clot for a minimum of one hour at room temperature. The clotted material is removed with sterile tweezers and any remaining solid material removed by centrifugation at 10,000×g for 10 minutes. Serum is stored in 500 ul aliquots at −80° C. until use.

Ponceau S stained membranes are completely destained by continuing to soak in water for an additional 10 minutes and placed in heat-sealable plastic bags or trays with 5 ml of blocking buffer (0.1% Tween 20 in 100 mM Tris-Cl, pH 7.5; 0.9% NaCl), for about 30 minutes at room temperature on an orbital shaker. Serum samples (including normal pre-immune rabbit serum control samples) are thawed, diluted at 1:100 to 1:10,000 in blocking buffer, and 5 ml added to the bags or trays along with fresh blocking buffer. The membranes are incubated for 30 minutes to overnight at room temperature in an orbital shaker. After incubation, the membranes are removed and washed in blocking buffer several times for about 15 minutes each with agitation. Commercially available alkaline-phosphatase conjugated anti-rabbit secondary antibody with fresh blocking buffer is added to the bags or trays which are incubated for one hour at room temperature in an orbital shaker. After incubation, the buffer is removed and the membranes treated according to the appropriate enzymatic visualization protocol.

Bands observed using seminal vesicle specific antiserum in the blood, urine, or semen sample that are also observed in the seminal vesicle sample, but not in the negative control samples or using normal rabbit serum are considered positive and likely candidates for use in the detection of prostatic neoplasia.

Example 2 - Isolation of Seminal Vesicle-Specific Markers

Figure 2B:
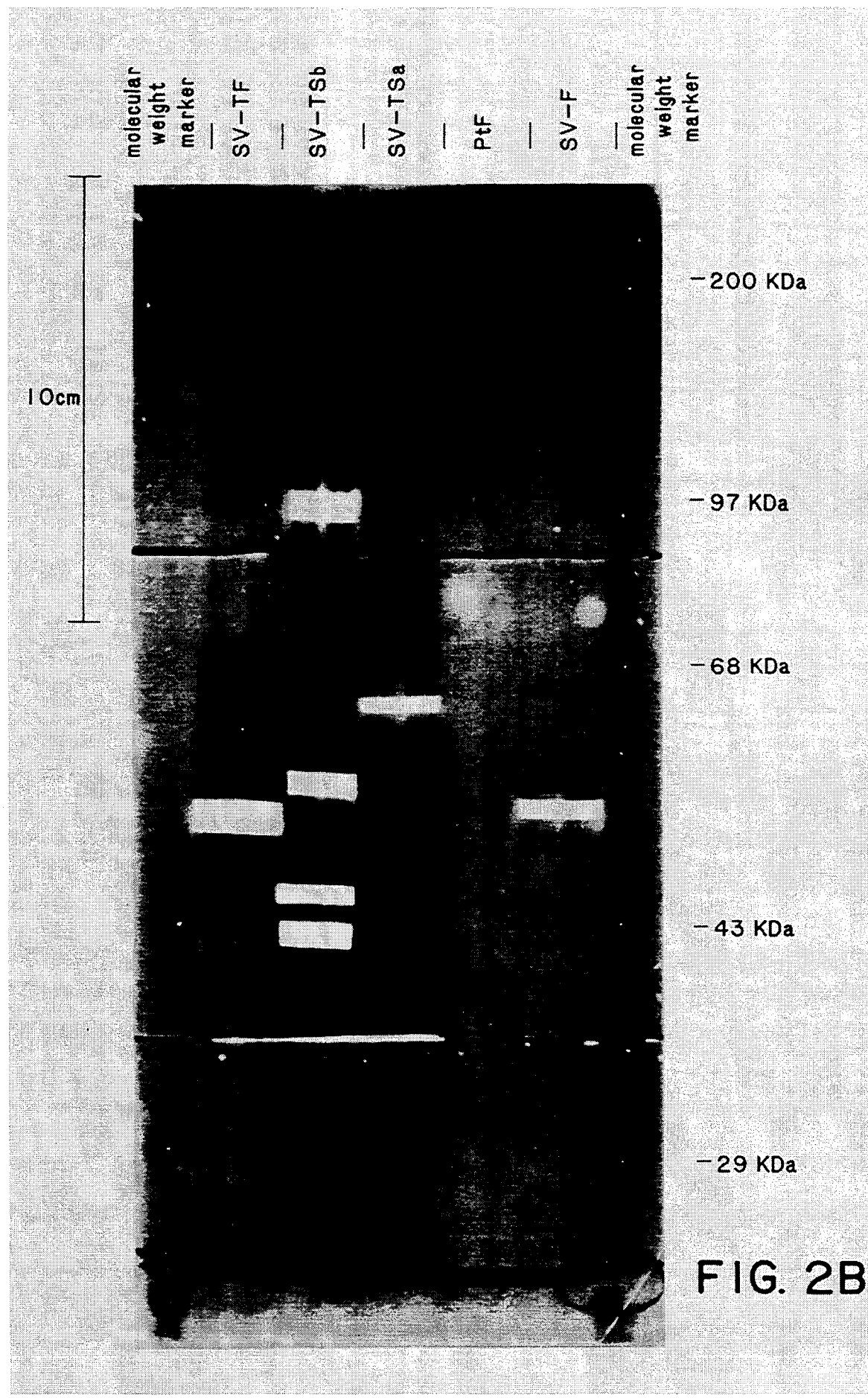
FIG. 2B Ponceau S stained nitrocellulose membrane of electrophoretically separated fractions of seminal vesicle tissue homogenate after excision of specific bands.

Positive bands visualized by Ponceau S staining in Example 1 are directly excised from the membrane (FIG. 2B). Excised bands are ground into a powder or dissolved in DMSO using the method of Kundson (K. A. Kundson, Proteins transferred to nitrocellulose for use as immunogen, Annual-Became. 147:285, 1985), mixed with incomplete Freund's adjuvant and injected into rabbits as described in Example 1 to generate specific antisera. The first antigen only is presented in complete Freund's adjuvant.

This antisera can be used directly to identify seminal vesicle-specific markers in patient samples, such as samples of blood, urine, or semen and are analyzed by Western blot or can be used to create immunoaffinity columns. Briefly, antisera is diluted to about 20 ug/ul in PBS. Two mils of serum are dialyzed against one liter of dialysis solution (100 mM NaHCO$_3$; 400 mM NaCl) at 4° C. for 24 hours with three solution changes. The dialyzed serum is centrifuged at 100,000×g for one hour to remove aggregates, the resulting supernatant is diluted to 5 mg/ml with dialysis solution, and the clarified serum stored at 4° C. Commercially available cyanogen bromide (CNBr) activated Sepharose is prepared according to the appropriate protocol and coupled with the antibodies of the serum. The percent coupling is determined and the antibody-coupled Sepharose stored at 4° C. in TSA buffer (10 mM Tris-Cl, pH 8.0; 140 mM NaCl; 0.025% NAN$_3$) until use.

Appropriate fractions of seminal vesicle tissue or fluid, blood, or semen are prepared as before and added to columns of antiserum coupled Sepharose. The columns are washed with TSA buffer and eluted with 50 mM Tris-Cl, pH 6.8. Eluted samples are confirmed to be seminal vesicle-specific using the procedure described in Example 1. Fractions collected from the immunoaffinity columns are subjected to further purification using HPLC or reverse-phase HPLC.

Example 3 - Peptide Sequencing

Proteins isolated by band excision from HPLC analysis as described in Example 2 are analyzed for amino acid composition and sequence. Band-excised purified proteins or protease digested fractions of proteins are applied to a 470A gas phase protein sequenator (Applied Biosystems, Inc.) which is connected to an ABI 120 (HPLC) PTH analyzer. Amino acid sequences determined are compared to the GENBANK DNA and NBRF protein data bases on a Macintosh IIsi personal computer using MacVector version 4.0 software to determine if the proteins have been previously identified.

Based on the sequences determined, corresponding peptide sequences are prepared. Synthetic peptides are coupled to keyhole lymphocyte hemocyanin (KLH) using commercially available kits (Pierce Chem. Co.) to facilitate anti-peptide antibody production in rabbits or mice.

Example 4 - Production of Seminal Vesicle Marker-Specific Monoclonal Antibodies

Purified and synthetic proteins and peptides are individually intraperitoneally injected into Balb/c mice in an equal volume of incomplete Freund's adjuvant at a total volume of about 250 ul per injection. Identical booster injections are given at three-week intervals. Three days after the final booster, the mouse is sacrificed and the spleen removed and placed in a 100 mm sterile culture dish with about 10 ml of RPMI 1640 medium without serum. Spleen cells are teased and torn apart using a pair of 19 gauge needles and aspirated until the cells are fully dispersed. The cell suspension is allowed to sit for three minutes for large clumps to settle and the suspended cells removed. Cells are washed twice by centrifugation at 400×g in RPMI 1640 at 37° C. in the absence of serum. P3-X63Ag8 myeloma cells of equal number are also washed twice in serum free medium at 800×g. After the final wash, the two cell pellets (myeloma and spleen cells) are combined in serum-free medium pre-warmed to 37° C. and centrifuged at 800×g for 5 minutes. All medium is carefully removed from the pellet, which is suspended in a solution of 50% PEG by slowly adding the PEG while slowly stirring the cell pellet with the end of a piper for one minute. Stirring is continued for another minute. Pre-warmed serum free medium is added to the cell suspension slowly over the next 3 minutes to a total volume of 10 mils. Cells are centrifuged for 5 minutes at $800 \times g$ and resuspended in 10 mils of medium supplemented with 10% fetal calf serum. Cell suspensions of 100 ul each are transferred into wells of a 96-well microtiter plate, incubated at 37° C. in a 5% $CO_2$ incubator, and the fused cells selected. After about 7-10 days cell supernatants of the fused cells are screened for antibody specific to the seminal vesicle marker of interest and the selected populations expanded. Hybridomas are picked and cultured. Monoclonal antibody is used directly or stored at $-80°$ C. in 0.5 ml aliquots.

Example 5 - Identification and Isolation of Seminal Vesicle-Specific Marker Genes Polyclonal and monoclonal antibodies prepared in Examples 1, 2 and 4 are used to screen human seminal vesicle-specific cDNA expression libraries for seminal vesicle-specific marker proteins. Positive bacterial colonies or bacteriophage plaques are identified by Western blotting the supernatants of individual clones with antibody preparations. Positive clones are expanded and the recombinant DNA insert restriction mapped and sequenced using dideoxynucleotide chain termination methodology. These sequences are analyzed by computer alignment to available sequences in GEN BANK as in Example 3. DNA sequences of interest are subcloned into recombinant expression vectors for large scale production of seminal vesicle-specific marker. In addition, cDNA expression libraries are screened using $^{32}$P-radiolabeled oligonucleotides or DNA fragments as probes to either known genes, for example, semenogelin I, its three subunits, or semenogelin II, are prepared based on the peptide sequences obtained in Example 3. The oligonucleotide probes are synthesized to recognize peptide-encoding fragments enriched for the amino acid residues met, trp, phe, tyr, cys, his, gln, asn, lys, asp, and gln, in this order of priority. Such probes are capable of recognizing a minimum of 21 deoxynucleotide residues corresponding to a minimum length of seven amino acid residues.

Example 6 - Diagnostic Kits Containing Seminal Vesicle-Specific Marker.

Microtiter plates are fixed with the seminal vesicle-specific marker made recombinantly as in Example 5 or purified conventionally as in Example 2. To the fixed antigen are added samples of blood or urine obtained from both normal healthy volunteers, patients with non-prostatic forms of cancer, and patients with suspected or confirmed cases of prostatic neoplasia with varying stages of severity. The samples are incubated for one hour at room temperature in a total volume of about 100 ul, after which, all liquid is removed by flicking the plates. Plates are washed three times with PBS, after which commercially available alkaline phosphatase conjugated anti-human antibodies are added to each well and the solution treated according to the appropriate visualization protocol. If the biological samples of, for example, blood or urine, contain seminal vesicle-specific antibodies, the antisera will bind to the fixed antigen. Positive indications are determined by comparing the binding observed with samples from the prostatic neoplasia positive patients with baseline determinations made for binding observed with samples obtained from normal individuals or individuals with other forms of cancer.

Kits are also created using immuno-slot blots. Nitrocellulose membranes are placed in a slot blot apparatus and the various patient samples of serum, urine or semen, are placed individually in the slots and immobilized. Binding is detected using labeled seminal vesicle-specific marker or seminal vesicle-specific marker and a labeled secondary to detect bound marker and an appropriate visualization protocol. Alternatively, the marker protein may be bound to individual wells of the slot blot. Each well is cut with scissors to isolate immobilized antigen, immersed and incubated in patient samples, rinsed, and anti-human antibody conjugates applied to detect the complex. In addition to these methods, human antisera can be applied directly to Western blot membranes containing electrophoresed and transferred seminal vesicle components of homogenates or purified proteins. Following rinsing, anti-human antibody conjugates are applied to detect the complex.

Example 7 - Diagnostic Kits Containing Antibody Specific To Seminal Vesicle-Specific Markers Microtiter plates are fixed with anti-seminal vesicle-specific rabbit polyclonal or murine monoclonal antibody prepared as described in Examples 2 and 4, or human monoclonal antibody. Human monoclonal antibody is created by fusing human spleen cells, which were exposed to antigen, with human or partly human myeloma cells and selecting the appropriate hybridoma cells or by cloning the antibody binding site of a non-human antibody gene into the appropriate position of a human antibody expressing cell. To the fixed seminal vesicle-specific antibodies are added samples of blood, semen, or urine obtained from normal healthy volunteers, patients with non-prostatic forms of cancer, and patients with suspected and confirmed prostatic neoplasia with varying stages of severity. The plates are incubated for one hour at room temperature in a total volume of 100 ul. After one hour, the liquids in the samples are removed by flicking the plates dry and the plates washed three times with PBS. Alkaline-phosphatase conjugated secondary antibody is added and the plates are treated according to the appropriate visualization protocol. Positive indications are determined by comparing the binding observed with the samples obtained from prostatic neoplasia patients with a baseline binding level observed in samples taken from normal healthy volunteers and patients with non-prostatic forms of cancer.

Kits are also created using slot blots as in Example 6. Nitrocellulose membranes are placed in a slot blot apparatus and the various patient serum, urine, and semen samples, placed individually in the slots and immobilized. The amount of marker protein is determined using labeled seminal vesicle-specific antibody and an appropriate visualization protocol. In addition to these methods, the human samples are resolved on SDS PAGE gels and Western blotted using rabbit polyclonal, mouse monoclonal, or human monoclonal antibodies that recognize a specific marker protein. A secondary conjugated antibody is used to visualize the complex.

Other embodiments or uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A method of screening for prostatic neoplasia in a patient comprising the steps of:
   a. providing a seminal vesicle-specific marker,
   b. incubating the marker with a biological fluid sample from the patient suspected of containing antibody to the marker to form a mixture,
   c. determining the amount of bound antibody in the mixture, and
   d. comparing the amount of bound antibody with a predetermined base level.

2. The method of claim 1 wherein the prostatic neoplasia screened for is nodular hyperplasia, prostatic carcinoma, invasive prostatic carcinoma, or prostatic carcinoma which has metastasized.

3. The method of claim 1 wherein the patient is a human.

4. The method of claim 1 wherein the marker comprises a protein or a fragment of a protein.

5. The method of claim 4 wherein the protein or protein fragment is expressed from a recombinant vector.

6. The method of claim 1 wherein the marker is fixed to a solid support.

7. The method of claim 6 wherein the solid support is a plastic support selected from the group consisting of a tissue culture plate, a vial, a microtiter plate, a stick, a paddle, a beard, and a microbead.

8. The method of claim 1 wherein the biological fluid sample comprises blood, urine, or semen or tissue fluids.

9. The method of claim 1 wherein the amount of antibody in the sample is determined by incubating the mixture with a second antibody which binds to the seminal vesicle-specific antibody.

10. The method of claim 9 wherein the second antibody is labeled with a detectable label.

11. The method of claim 10 wherein the detectable label is selected from the group consisting of a radio isotope, a stable isotope, a fluorescent chemical, a luminescent chemical, a metal, an electrical charge, an enzyme, a chromatic chemical, a spatial chemical, an electron dense molecule, and a label detectable by mass spectrometry.

12. The method of claim 1 which is an EIA, an ELISA, a Western blot, a slot blot, or a RIA.

13. The method of claim 1 wherein the amount of antibody in the mixture is determined by a direct assay, an indirect assay, a competition assay, an inhibition assay, or a combination of these assays.

14. A kit for screening for prostatic neoplasia in a patient comprising one or more purified or partially purified seminal vesicle-specific markers fixed to a solid support and a labeled secondary antibody specific to human immunoglobulin.

15. A method of screening for prostatic neoplasia in a patient comprising the steps of:
   a. providing a first antibody which specifically binds a seminal vesicle marker,
   b. incubating the antibody with a biological fluid sample from the patient to form a mixture,
   c. determining the amount of antibody-bound marker in the mixture, and
   d. comparing the amount of bound marker determined with a predetermined base level.

16. The method of claim 15 wherein the prostatic neoplasia screened for is nodular hyperplasia, prostatic carcinoma, invasive prostatic carcinoma, or prostatic carcinoma which has metastasized.

17. The method of claim 15 wherein the patient is a human.

18. The method of claim 15 wherein the marker comprises a protein or protein fragment.

19. The method of claim 15 wherein the antibody is a monoclonal antibody or a monoclonal antibody fragment.

20. The method of claim 19 wherein the monoclonal antibody or monoclonal antibody fragment is of an IgG isotype.

21. The method of claim 20 wherein the monoclonal antibody fragment is an Fv fragment.

22. The method of claim 15 wherein the antibody is a polyclonal antibody or a polyclonal antibody fragment.

23. The method of claim 22 wherein the polyclonal antibody fragment is an Fv fragment.

24. The method of claim 15 wherein the antibody is fixed to a solid support.

25. The method of claim 24 wherein the solid support is a plastic selected from the group consisting of a tissue culture plate, a vial, a microtiter plate, a stick, a paddle, a bead, or a microbead.

26. The method of claim 15 wherein the biological fluid sample comprises blood, urine, semen or tissue fluids.

27. The method of claim 15 wherein the amount of bound marker in the sample is determined by incubating the mixture with a second antibody which specifically binds to the marker.

28. The method of claim 27 wherein the first or the second antibody is labeled with a detectable label.

29. The method of claim 28 wherein the detectable label is selected from the group consisting of a radio isotope, a stable isotope, a fluorescent chemical, a luminescent chemical, a metal, an electrical charge, an enzyme, a chromatic chemical, a spatial chemical, an electron-dense molecule, and a label detectable by mass spectrometry.

30. The method of claim 15 which is an EIA, an ELISA, a Western blot, a slot blot, or a RIA.

31. The method of claim 15 wherein the amount of marker in the mixture is determined by a direct assay, an indirect assay, a competition assay, an inhibition assay, or a combination of these assays.

32. A diagnostic kit for the detection of prostatic neoplasia in a patient comprising
   (a) one or more antibodies or fragments thereof which specifically bind seminal vesicle-specific markers, said antibodies or fragments being fixed to a solid support, and
   (b) a labeled secondary anybody which specifically binds seminal vesicle-specific markers.

33. The method of claim 1 wherein the prostatic neoplasia screened for is prostatitis.

34. The method of claim 15 wherein the prostatic neoplasia screened for is prostatitis.

* * * * *